United States Patent [19]

Kriesel et al.

[11] Patent Number: 5,693,018
[45] Date of Patent: Dec. 2, 1997

[54] SUBDERMAL DELIVERY DEVICE

[75] Inventors: Marshall S. Kriesel, St. Paul; Farhad Kazemzadeh, Bloomington; Matthew B. Kriesel, St. Paul, all of Minn.; William W. Feng, Lafayette, Calif.; Steve C. Barber, Shorewood, Minn.; William J. Kluck, Hudson, Wis.

[73] Assignee: Science Incorporated, Bloomington, Minn.

[21] Appl. No.: 541,030

[22] Filed: Oct. 11, 1995

[51] Int. Cl.⁶ ........................................... A61M 37/00
[52] U.S. Cl. ...................... 604/132; 604/246; 604/890.1; 128/DIG. 12
[58] Field of Search ........................ 604/131–132, 604/153, 246, 257, 263, 890.1; 128/DIG. 12

[56] References Cited

U.S. PATENT DOCUMENTS

| | | | |
|---|---|---|---|
| 3,918,446 | 11/1975 | Buttaravoli | 128/133 |
| 4,380,234 | 4/1983 | Kamen | 604/130 |
| 4,505,702 | 3/1985 | Perry et al. | 604/209 |
| 4,619,652 | 10/1986 | Eckenhoff et al. | 604/415 |
| 4,753,651 | 6/1988 | Eckenhoff et al. | 604/896 |
| 4,886,499 | 12/1989 | Cirelli et al. | 604/131 |
| 5,176,662 | 1/1993 | Bartholomew et al. | 604/283 |
| 5,257,980 | 11/1993 | Van Antwerp et al. | 604/282 |
| 5,390,671 | 2/1995 | Lord et al. | 128/635 |

FOREIGN PATENT DOCUMENTS

WO9513838  5/1995  WIPO .

Primary Examiner—Corrine M. McDermott
Attorney, Agent, or Firm—James E. Brunton

[57] ABSTRACT

An apparatus for accurately infusing fluids into a patient at specific rates over an extended period of time. The apparatus is of a low profile, laminate or layered construction having a stored energy source in the form of a distendable membrane, which, in cooperation with the base of the apparatus, defines one or more fluid reservoirs, each having a fluid inlet and a fluid outlet. The apparatus further includes, a high novel, conformable ullage made of yieldable materials. The conformable ullage uniquely conforms to the shape of elastomeric membrane as the membrane returns to its less distended configuration. Additionally, the infusion cannula of the apparatus is connected to the base in a novel manner which permits expeditious subdermal delivery to the patient via a cannula which extends generally perpendicularly relative to the base. The cannula is connected to the base in a manner such that the pierceable portion of the cannula is free to move relative to the base of the device in response to movements by the patient which cause flexing of the muscle and tissue in the vicinity of the cannula.

23 Claims, 9 Drawing Sheets

SUBDERMAL DELIVERY DEVICE

BACKGROUND OF THE INVENTION

This appliction is related to co-pending application, Ser. No. 08/451,520 filed May 26, 1995, is also related to a Continuation-In-Part application to Ser. No. 08/451,520 filed on even date herewith.

FIELD OF THE INVENTION

The present invention relates generally to fluid delivery devices. More particularly, the invention concerns an improved device for subdermal infusion of agents into an ambulatory patient at specific rates over extended periods of time.

DISCUSSION OF THE INVENTION

A number of different types of liquid dispensers for dispensing medicaments to ambulatory patients have been suggested. Many of the devices seek either to improve or to replace the traditional hypodermic syringe which has long been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range. Conventional therapy involves injecting insulin by syringe several times a day, often coinciding with meals. The dose must be calculated based on glucose levels present in the blood. If the dosage is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.3–3 mL depending on body mass) over comparatively long periods of time (18–24) hours). As will be appreciated from the discussion which follows, the apparatus of the present invention is uniquely suited to provide precise fluid delivery management at a low cost in those cases where a variety of precise dosage schemes are of utmost importance.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices is provided in the form of a semi-rigid structure having flow channels leading from the top of the structure through the base to inlet or outlet ports of the device. Since the inventions described herein represent improvements over those described in U.S. Pat. No. 5,205,820, this patent is hereby incorporated by reference as though fully set forth herein.

In the rigid ullage configuration described in U.S. Pat. No. 5,205,820, the stored energy means of the device must be superimposed over the ullage to form the fluid-containing reservoir from which fluids are expelled at a controlled rate by the elastomeric membrane of the stored energy means tending to return to a less distended configuration in the direction toward the ullage. With these constructions, the stored energy membrane is typically used at high extensions over a significantly large portion of the pressure-deformation curve.

For good performance, the elastomeric membrane materials selected for construction of the stored energy membrane must have good memory characteristics under conditions of high extension; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits must less effect on the total fluid delivery profile, but in very small dosages, the tail-off volume becomes a larger portion of the total volume. This sometimes places severe physical limits on the range of delivery profiles that may easily be accommodated using the rigid ullage configuration.

As will be better appreciated from the discussion which follows, the apparatus of the present invention provides a unique and novel improvement for a disposable dispenser of simple but highly reliable construction that may be adapted to many applications of use. A particularly important aspect of the improved apparatus is the incorporation of conformable ullages made of yieldable materials which uniquely conform to the shape of the stored energy membrane as the membrane distends and then returns to a less distended configuration. This novel construction will satisfy even the most stringent delivery tolerance requirements and elegantly overcomes the limitation of materials selection.

Another useful liquid delivery device is that described in U.S. Pat. No. 5,226,896 issued to Harris. This device comprises a multidose syringe having the same general appearance as a pen or mechanical pencil. the device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device which is compact, is easy to use by ambulatory patients, and is eminently capable of meeting the most stringent of fluid delivery tolerance requirements.

SUMMARY OF THE INVENTION

It is an object of the present invention to provide an apparatus having a self-contained stored energy membrane for expelling fluids at a precisely controlled rate which is of a compact, extremely low profile, laminate construction. More particularly, it is an object of the invention to provide such an apparatus which is of very low profile so that it can conveniently be used for the precise delivery of pharmaceutical fluids, such as insulin solution and the like, into an ambulatory patient at controlled rates over extended periods of time.

It is another object of the invention to provide an apparatus of the aforementioned character which is highly reliable and easy-to-use by lay persons in a non-hospital environment.

It is another object of the invention to provide an apparatus as described in the preceding paragraphs which, can be used for subdermal infusion of fluids. In this regard, the apparatus includes a novel and unique delivery cannula having a body portion disposed within a circuitous channel formed within the base superstructure of the apparatus and a pierceable portion which extends outwardly from the base of the apparatus. The cannula is mounted within the circuitous channel in a manner such that the pierceable portion is free to move in three axes thereby permitting the outwardly extending end portion to move relative to the base in response to forces exerted thereon due to normal movements by the patient which cause flexing of the muscle and tissue in the area of the cannula.

Another object of the invention is to provide an apparatus which embodies a soft, pliable, conformable mass which defines an ullage within the reservoir of the device which will closely conform to the shape of the stored energy membrane thereby effectively avoiding extended flow delivery rate tail-off at the end of the fluid delivery period.

A further object of the invention is to provide a low profile, fluid delivery device of laminate construction which can meet even the most stringent fluid delivery tolerance requirements.

Another object of the invention is to provide an apparatus of the character described which, due to its unique construction, can be manufactured inexpensively in large volume by automated machinery.

Other objects of the invention are set forth in U.S. Pat. No. 5,205,820 which is incorporated herein by reference and still further objects will become apparent from the discussion which follows.

DESCRIPTION OF THE INVENTION

Figure 1:
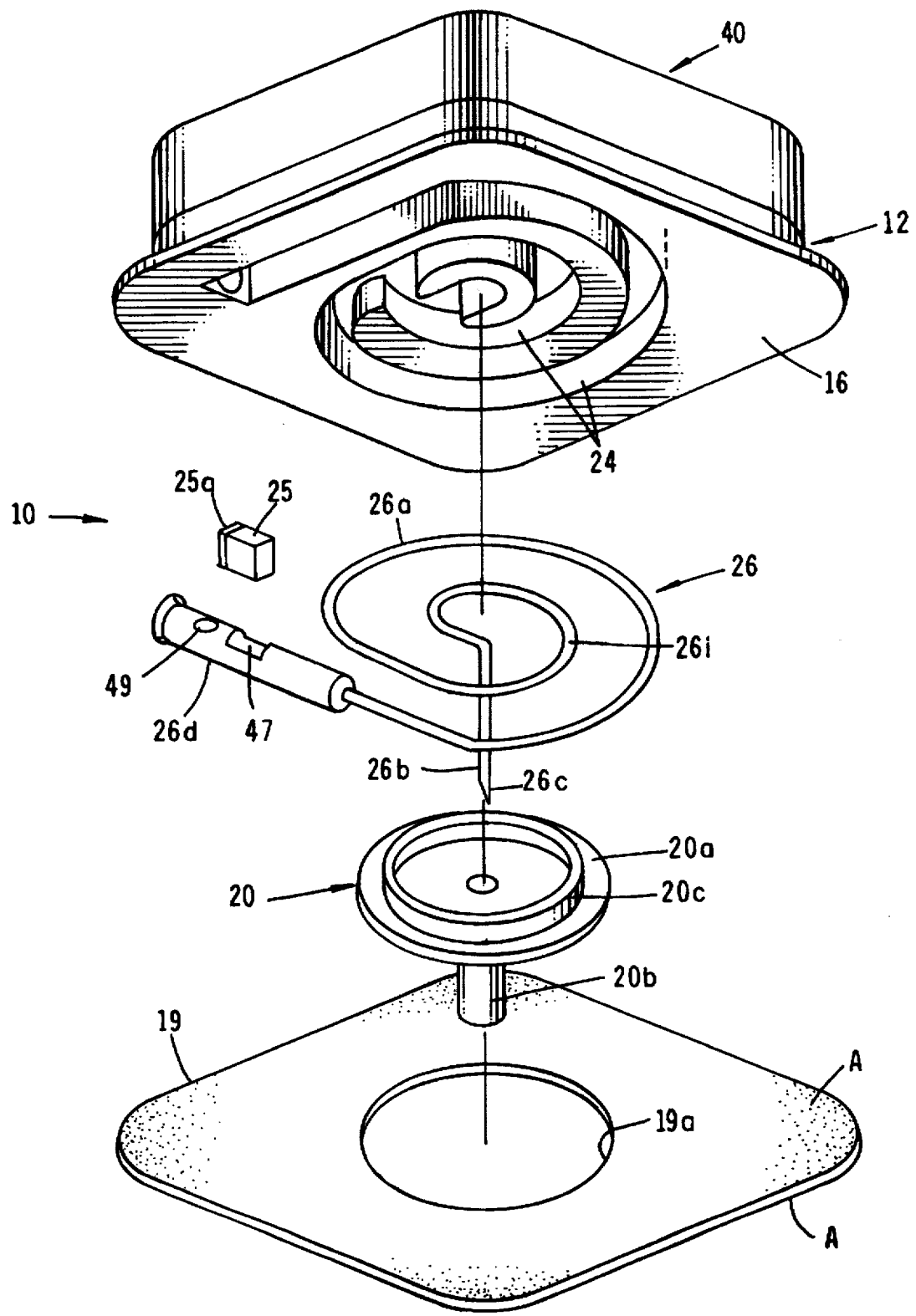
FIG. 1 is a generally perspective exploded view of one embodiment of the subdermal delivery device of the present invention.
Figure 2:
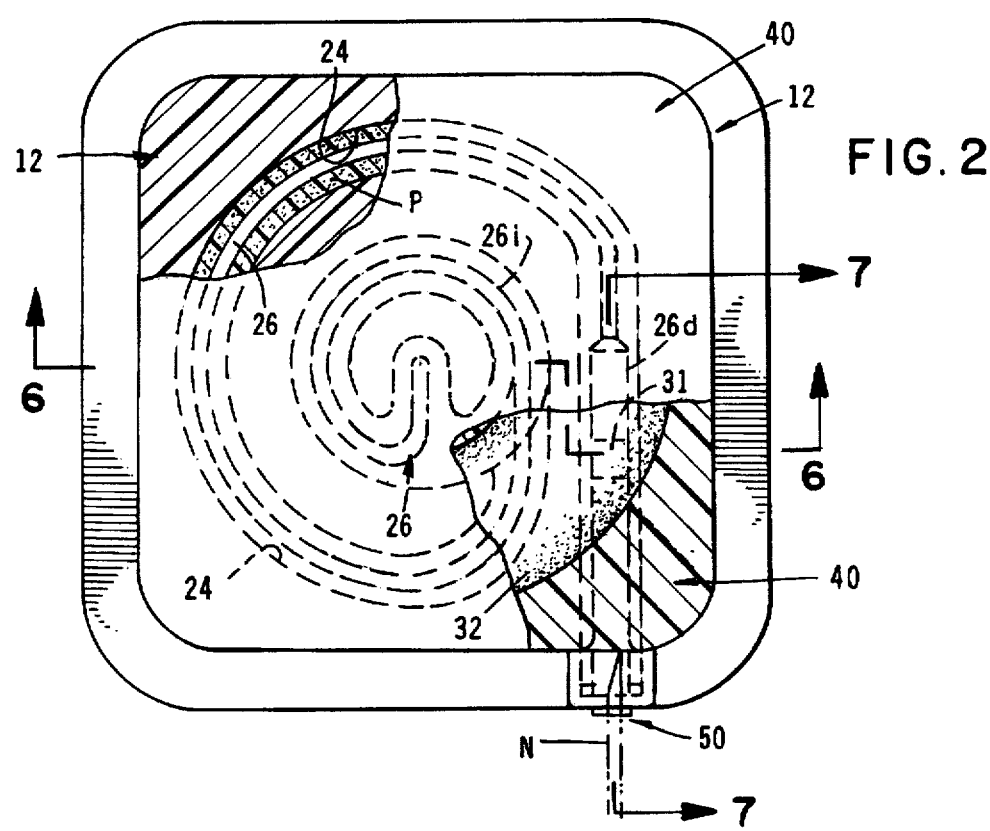
FIG. 2 is a top plan view of the invention shown in FIG. 1 and is broken away to show internal construction.

Referring to FIGS. 1 through 7, one form of the ultra low profile subdermal delivery device of the invention is there shown and generally designated by the numeral 10. The device comprises a base 12, having an upper surface 14 including a central portion 14a and a peripheral portion 14b circumscribing central portion 14a. As best seen in FIG. 1, base 12 is provided with a lower surface 16 to which a patient interconnection means or member 19 is connected.

Member 19 functions to releasably interconnect the device to the patient and includes an aperture 19a. Provided on both sides of member 19 is an adhesive layer "A" the purpose of which will presently be described.

Figure 4:
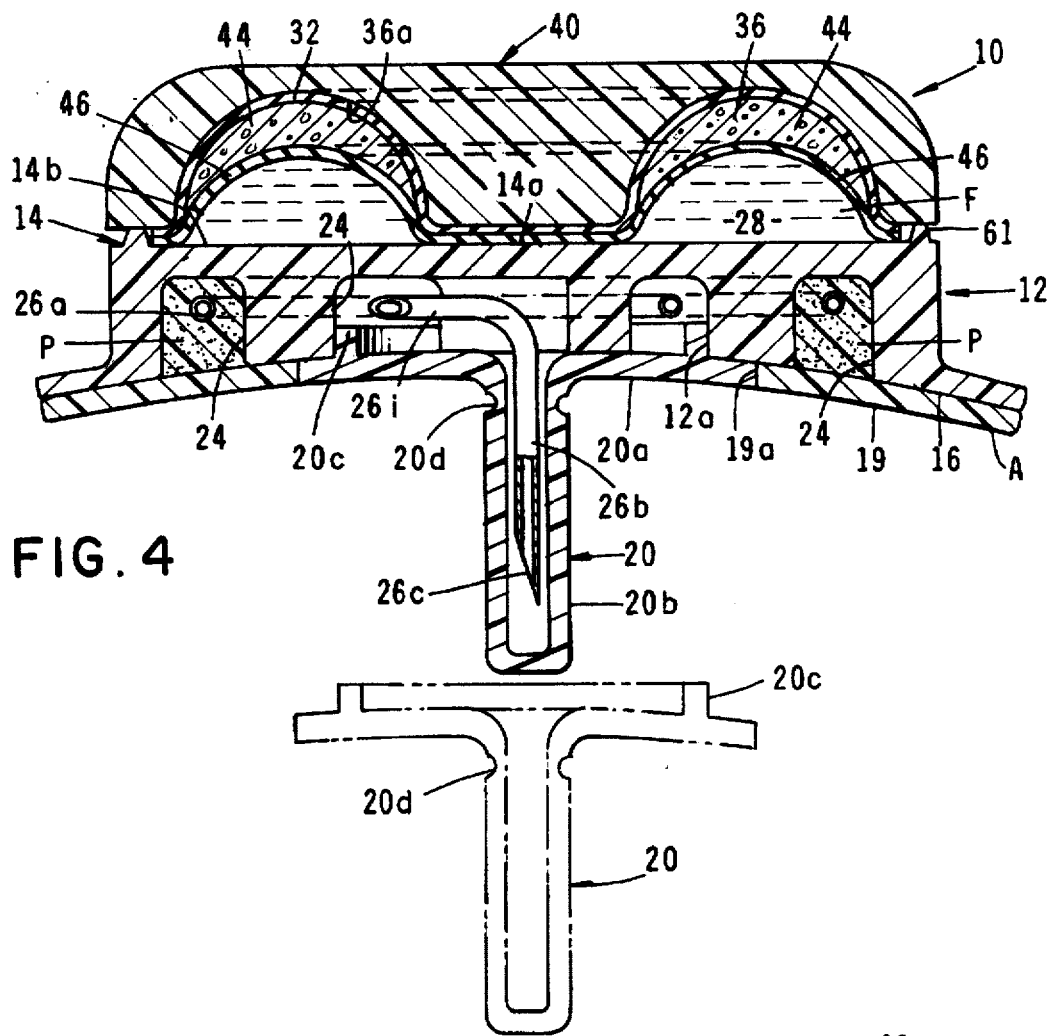
FIG. 4 is a cross-sectional view taken along lines 4—4 of FIG. 3.
Figure 5:
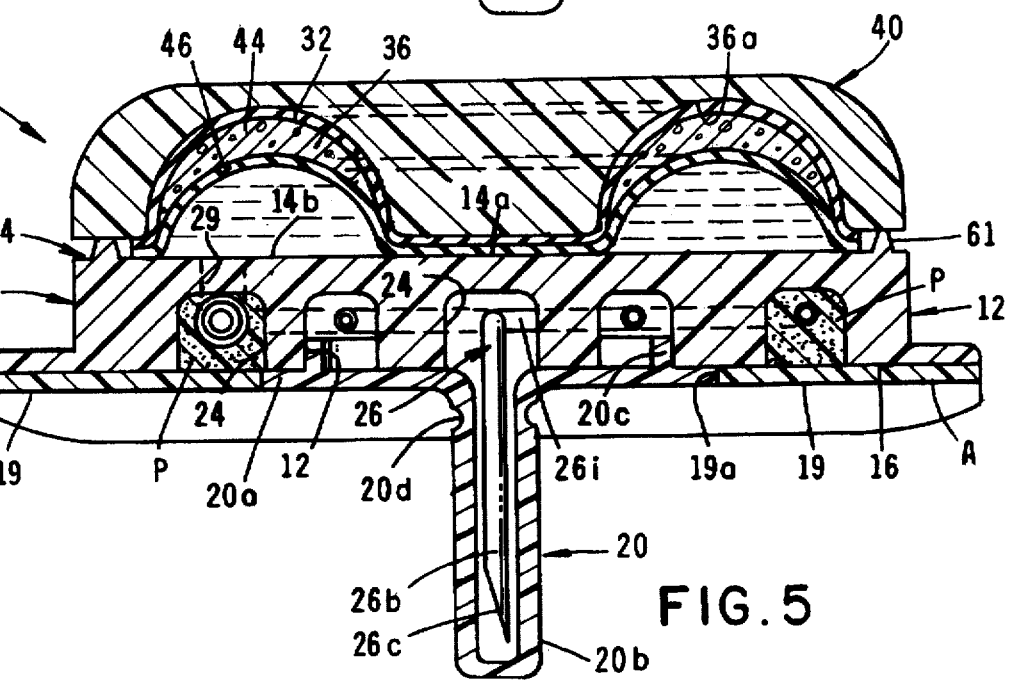
FIG. 5 is a cross-sectional view taken along lines 5—5 of FIG. 3.

To cover and protect the downwardly extending portion of the hollow cannula of the device is a sheath subassembly 20 having a generally circular base 20a which is receivable within aperture 19a of member 19 in the manner shown in FIGS. 4 and 5. Subassembly 20 also includes an upstanding rim 20c which is receivable within an opening 12a formed in base 12 (FIG. 4). Depending from base 20a of the sheath subassembly is a tear-away needle cover 20b which can be separated from base 20a along a serration 20d (FIG. 4).

Figure 6:
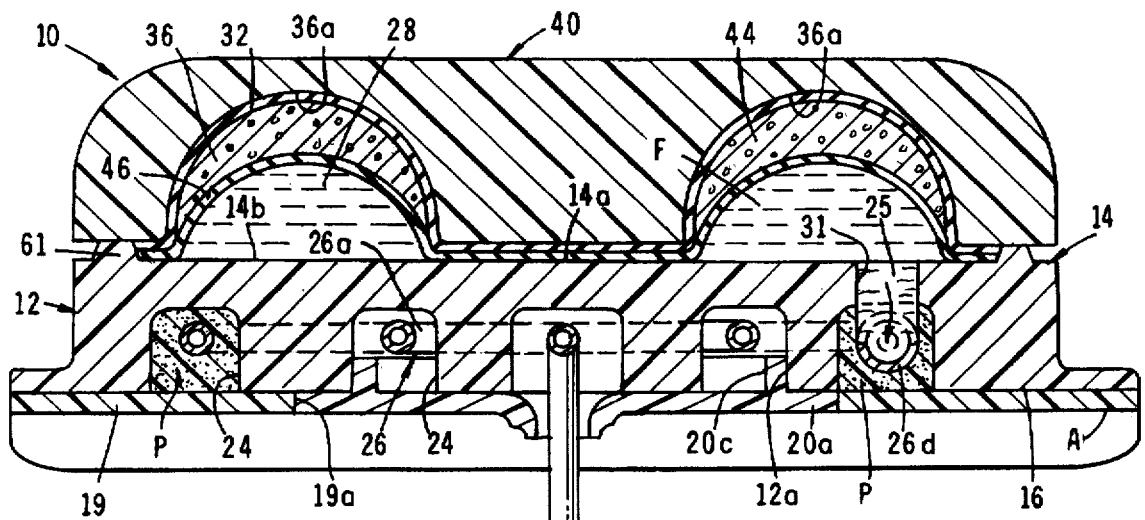
FIG. 6 is an enlarged, cross-sectional view taken along lines 6—6 of FIG. 2.
Figure 7:
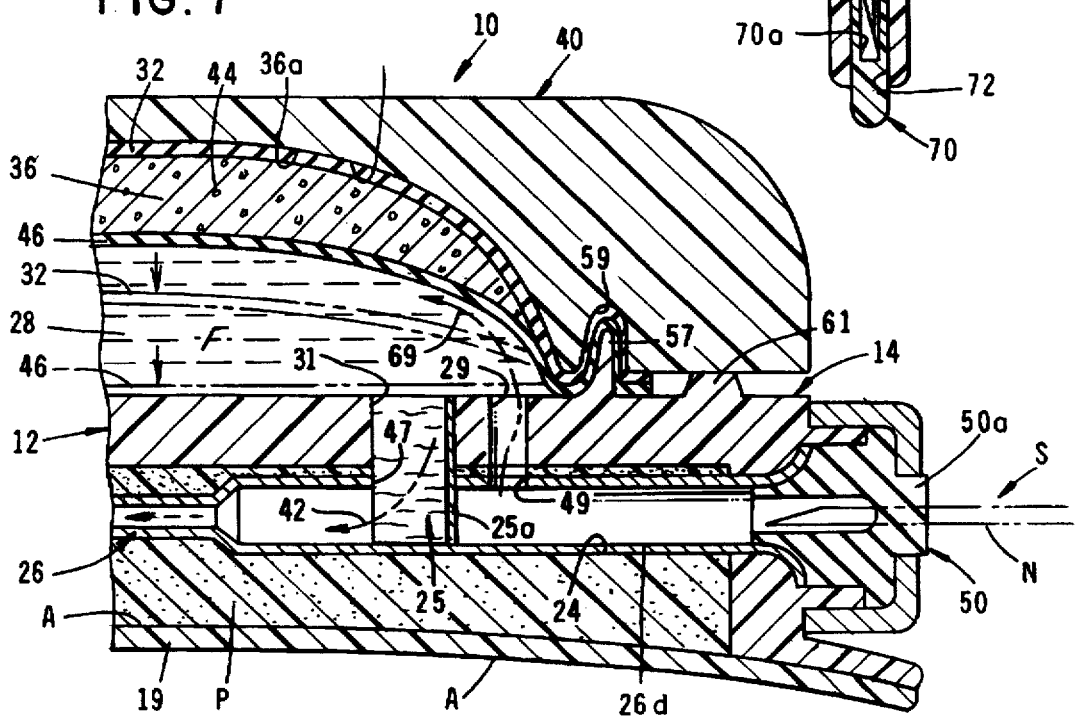
FIG. 7 is a greatly enlarged, cross-sectional view taken along lines 7—7 of FIG. 2.

Formed within base 12 is a circuitous channel 24 (FIG. 1) within which a novel spiral-like hollow cannula or capillary 26 is uniquely mounted in a manner presently to be described. A stored energy means cooperates with the upper surface 14 of base 12 to form a fluid reservoir 28 having an inlet port 29 and an outlet port 31 (FIG. 7) which is disposed proximate channel 24 in the manner shown in FIGS. 1 and 7. The stored energy means is here provided in the form of at least one distendable membrane 32 which is superimposed over base 12. Membrane 32 is distendable as a result of pressure imparted on the membrane by fluids "F" introduced into fluid reservoir 28 through port 29 (FIGS. 6 and 7). As membrane 32 is distended, internal stresses will be established, which stresses tend to move the membrane toward a less distended configuration and in a direction toward base 12. A unique feature of this latest embodiment of the invention resides in the fact that the reservoir or chamber 36, which includes fluid reservoir 28, is generally toroidal in shape with the outer boundary thereof being defined by a surface 36a formed in a cover member 40.

Provided within the toroidal-shaped reservoir 36 is ullage defining means for providing ullage within reservoir 36. In the embodiment of the invention shown in FIGS. 3 through 7, this ullage defining means comprises a conformable mass which substantially conforms to the shape of the distendable membrane as the membrane is distended and as it returns toward its less distended original configuration. More particularly, as the distendable membrane returns toward its less distended configuration, the conformable ullage will conformably follow its movement toward engagement with the upper surface 14 of base 12 and fluid contained within the reservoir will flow uniformly outwardly of the device through port 31 in the direction of the arrow 42 of FIG. 7.

The stored energy means, while shown in the drawings as a single distendable membrane 32, can comprise a laminate construction made up of a plurality of layers of elastomeric materials. The conformable ullage, which is identified in the drawings by the numeral 44, can be constructed from a number of materials such as various types of gels, fluids, gases, foams, and soft elastomers. Here the conformable ullage comprises a gel which is encapsulated between a barrier membrane 46 and distendable membrane 32 in the manner best seen in FIG. 4. Materials suitable for use in constructing the base, the cover, and the distendable membrane are discussed in detail in U.S. Pat. No. 5,205,802 which is incorporated herein by reference.

Referring particularly to FIG. 1, in the present form of the invention, the infusion means for infusing medicinal fluids from reservoir 28 into the patient comprises the previously identified circuitously shaped hollow cannula 26, which includes a body portion 26a which is mounted within circuitous channel 24 in a highly novel manner presently to be described. Flow control means, including filter means, here provided as a porous filter 25 having a fluid impermeable layer 25a, is disposed between the outlet 31 of reservoir 28 and an inlet 47 formed in the enlarged diameter portion 26d of cannula 26. Also formed in the enlarged diameter portion 26d of cannula 26 is an outlet port 49 which communicates with inlet 29 of reservoir 28. Cannula 26 also includes an outlet end 26b, here provided in the form of a needle-like segment, which extends generally perpendicularly downward from surface 16 of base 12 for subdermal infusion of medicinal fluids into the patient. For this purpose, segment 26b is provided with a sharp, pointed extremity 26c (see also FIG. 6). As previously discussed, sheath 20b surrounds and protects portions 26b and 26c of the cannula (FIG. 4).

Figure 3:
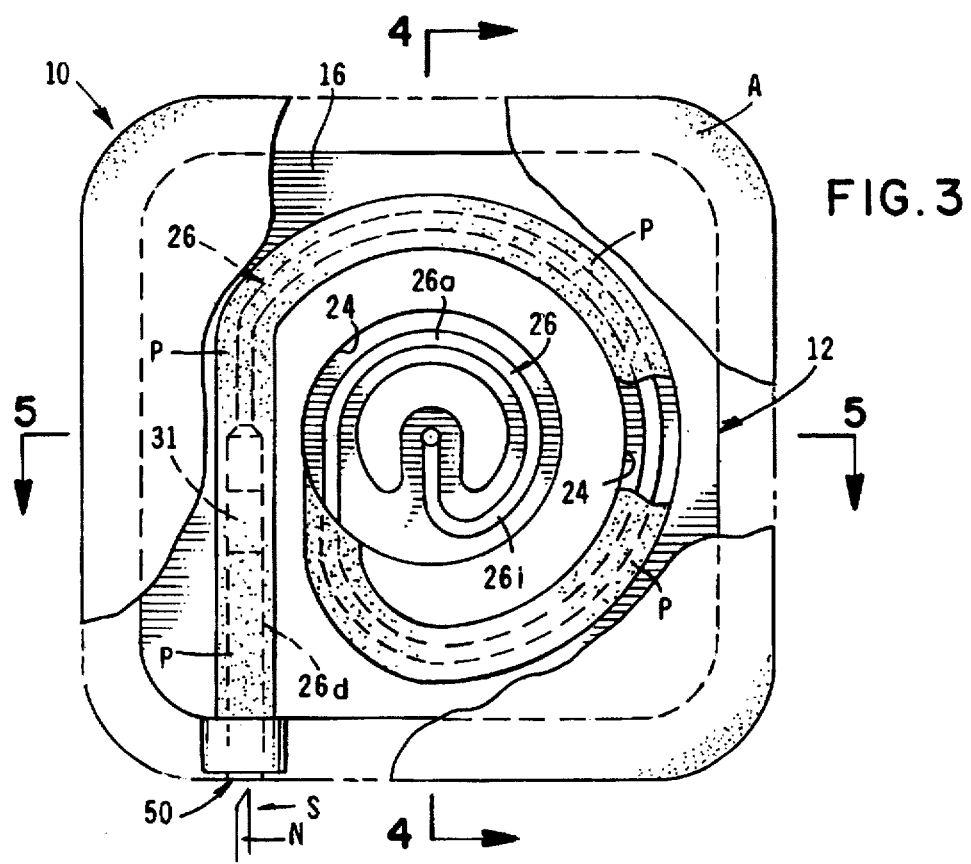
FIG. 3 is a bottom view of the apparatus shown in FIG. 1, again partly broken away to show internal construction.

Filling of reservoir 28 is accomplished in the manner previously described by introducing fluid into the reservoir under pressure via a septum assembly 50 mounted in base 12 (FIGS. 3 and 7). Using a conventional syringe assembly "S", fluid can be introduced into the enlarged diameter portion 26d of cannula 26 via the septum assembly 50. During this filling step, a barrier membrane 46 is distended outwardly against the conformable ullage 44 controllably moving it along with a distendable membrane 32 toward surface 36a of cover 40. As the ullage defining means moves toward cover 40, distendable membrane 32 will engage surface 36a and the ullage defining means will uniquely conform to the geometry of surface 36a as well as to the continuously varying geometry of distendable membrane 32. With this construction, when the fluid is dispensed from the device, the conformable ullage will permit the distendable membrane to provide a constant fluid expelling pressure on the fluid contained within the reservoir throughout the fluid delivery cycle, thereby avoiding undesirable delivery rate tail off at the end of the delivery period which is sometimes found in rigid ullage type devices of the character described in U.S. Pat. No. 5,205,820. This novel, substantially linear performance permits the device to meet even the most stringent medicinal fluid delivery requirements.

As best seen in FIG. 7, during the fluid delivery step, fluid will flow from reservoir 28, through port 31, through a flow control means and then into the enlarged diameter portion 26d of cannula 26. The flow control means here comprises the previously identified filter means, or filter 25, which can be constructed from various porous materials including a porous polycarbonate material available from Corning Costar Corporation and like suppliers. After flowing through the flow control assembly, the fluid will flow outwardly of the device via the hollow cannula 26 in the manner shown in FIG. 6.

Distendable member 32, along with barrier membrane 46 are secured to base 12 in any suitable manner such as by clamping the members between base 12 and cover 40. In this regard, as best seen in FIG. 7, the peripheral portion of base 12 is provided with an upstanding, generally circularly shaped tongue 57 which is received within a groove 59 provided in cover assembly 40 as the cover assembly mateably engages base 12. Base 12 is also provided with an upstanding, circumferentially extending membrane cutting means or protuberance 61 (FIG. 7), which is crushed in the manner shown in FIG. 7 as the cover and base are joined. Protuberance 61 functions to cleanly cut both distendable membrane 32 and barrier membrane 46 upon the cover assembly being brought into pressural engagement with the base. Protuberance 61 also uniquely functions as a sonic energy director for the sonic weldment of base 12 and cover 40. With this construction, following cutting of the distendable membrane and the barrier membrane, the cover can be sonically welded to the base in the proximity of the upstanding tongue of the base and the mating groove in the cover by techniques well understood by those skilled in the art. After the sonic welding step, the cover, the distendable membrane, and the barrier membrane are all interconnected with the base in a manner to provide a tightly sealed enclosure.

Turning once again to FIGS. 3, 4 and 5, it can be seen that part of the body portion of spiral cannula 26 is uniquely supported within channel 24 of base 12 by a cannula encapsulation means shown here as a standard potting compound "P". Compound "P" rigidly supports the body portion of the cannula within channel 24 and dynamically supports the outer extremity of the cannula body so that the spring-like portion 26i thereof (FIGS. 3 and 5) is free to move three dimensionally within channel 24. With this highly novel construction, when the device is connected to the patient with the needle portion 26b of the cannula penetrating the patient's body, as, for example, the patient's arm or leg, normal movement by the patient will permit the cannula to move within a portion of channel 24 while the base remains completely stationary. Without this important feature, normal movements by the patient causing flexing of the muscle and tissue would impart loosening forces to the device which, in time, could cause the adhesive pad "A" provided on the base of the device to separate from the patient's skin.

With the cannula enclosure subassembly 20 in position over cannula segment 26b, the reservoir of the device can be filled with the beneficial agent to be infused through use of a standard syringe assembly "S" having a needle "N" adapted to penetrate the septum 50a of the septum assembly 50 (FIG. 7). Fluid flowing under pressure from the syringe will enter the enlarged diameter portion 26d of cannula 26 and flow in the direction of the arrow 69 in FIG. 7 inwardly of port 29 and toward the fluid reservoir of the device. As the fluid under pressure flows into the fluid reservoir, barrier membrane 46 will be distended outwardly against the conformable ullage 44 in a manner to cause distendable membrane 32 to move into engagement with the inner surface 36a of the toroidal-shaped chamber formed in cover 40.

After the reservoir of the apparatus has been filled with the appropriate beneficial agent, the needle cap or covering 20b can be separated from the assemblage 20 by breaking it along the serration 20d (FIG. 4). This done, the device can be readily interconnected with the patient by penetrating the patient's skin with the sharp point 26c of the infusion cannula 26. As the patient's skin and tissue is penetrated by the infusion needle, the adhesive pad "A" provided on the lower surface of member 19 will cause the base of the device to securely adhere to the patient's skin. At the same time the adhesive layer formed on the upper surface of member 19 will securely bond member 19 to the lower surface of the base. In some instances, it is desirable to provide a protective peel layer over the lower adhesive layer on the lower surface of the device until time of use. In such instances, the protective layer is peeled from the lower surface of member 19 immediately prior to penetrating the patient's skin with point 26c of the infusion cannula.

As previously mentioned, the highly novel manner in which the very small diameter cannula 26 is mounted within channel 24 formed in base 12 permits the central portion 26i of the infusion cannula to move three dimensionally relative to the base within the limits of channel 24. This important feature enables the base of the device to remain stationary even though movement of the patient's extremities, which cause flexing of the muscles, skin, and tissue, tend to impart forces on the needle portion of the cannula, which, but for its ability to free float within channel 24, would cause loosening of the device relative to the patient's skin.

With the device securely interconnected with the patient, and with sheath 20b separated from base 20a of assembly 20, distendable membrane 32 will tend to return to its less distended configuration. As the distendable membrane moves toward base 12, the conformable ullage 44 will closely conform to its inner surface geometry thereby assuring a complete and substantially linear flow of fluid from the chamber, through the cannula 26, and into the patient.

Figure 5A:
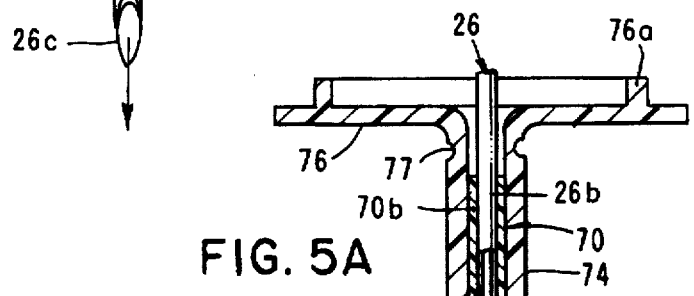
FIG. 5A is a greatly enlarged, cross-sectional view of the protective shield assembly of the invention which surrounds and protects the pierceable end portion of the cannula.

Referring to FIG. 5A, an alternate form of needle cover is there illustrated. This form of the needle cover is similar to that just described save for the fact that a protective sheath assembly further includes a closure means or cap 70 having an inner bore 70a within which cannula portion 26b is sealably received. The outer surface 70b of cap 70 is telescopically received within a central bore 72 provided in the downwardly protruding stem-like extremity 74 of the sheath assembly in the manner shown in FIG. 5A. It is to be noted that the sheath assembly of this form of the invention also includes a portion 76 which is receivable within aperture 19a provided in base portion 19. With this construction, cap 70 prevents fluid flow from the hollow cannula until the sheath is broken away along a serration 77 and cap 70 is removed from extremity 26b of the infusion cannula. An upstanding rim 76a is, as before, receivable within opening 12a of base 12.

Figure 8:
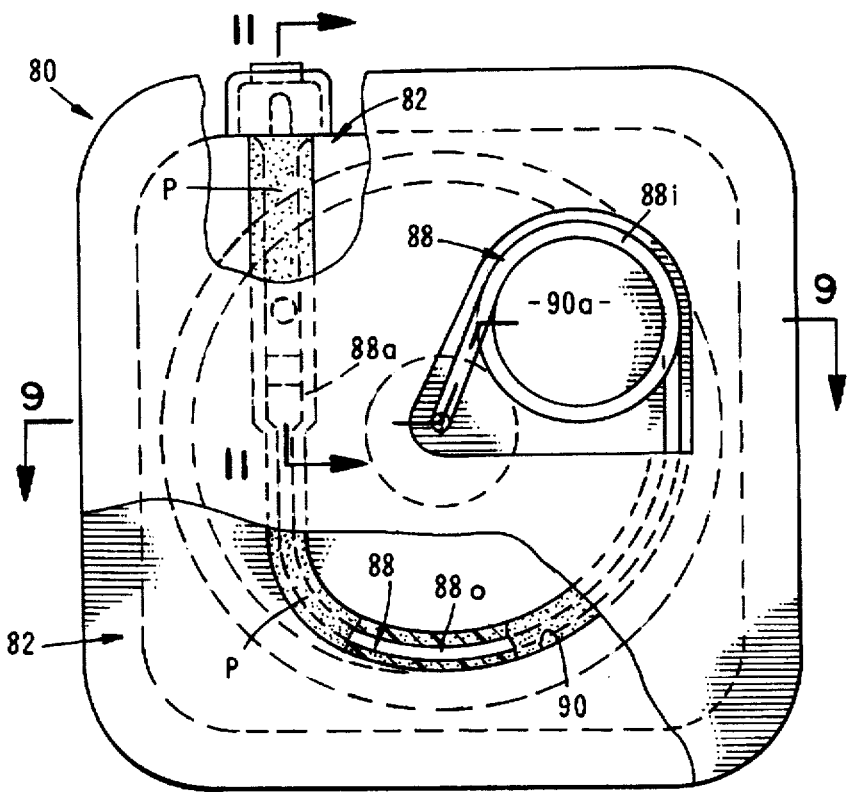
FIG. 8 is a bottom plan view of another form of the invention partly broken away to show internal construction.
Figure 9:
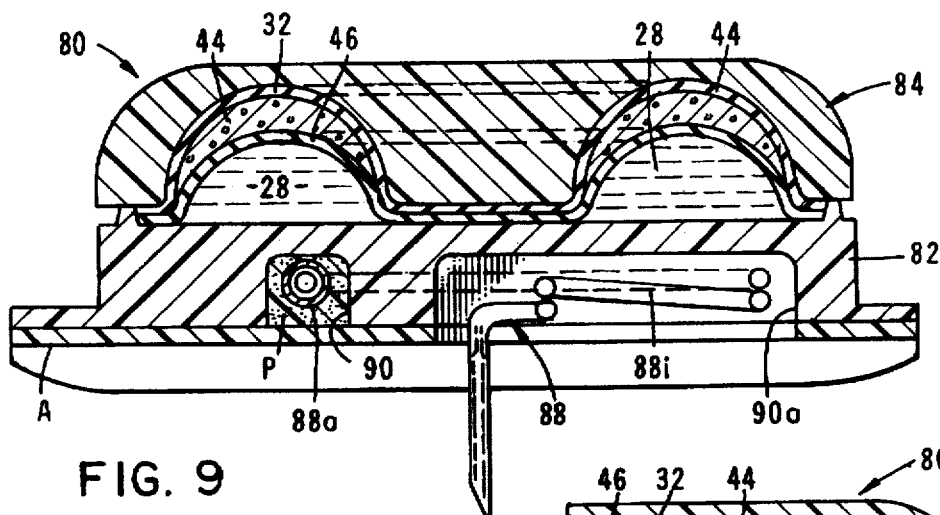
FIG. 9 is a cross-sectional view taken along lines 9—9 of FIG. 8.
Figure 11:
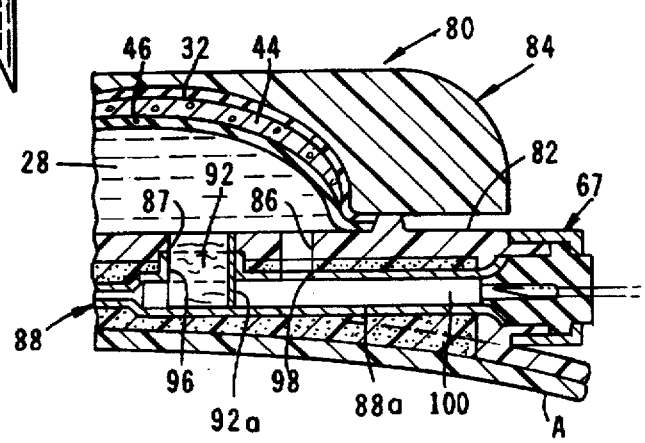
FIG. 11 is a cross-sectional view taken along lines 11—11 of FIG. 8.

Turning to FIGS. 8, 9, and 11, still a further form of the ultra low profile subdermal infusion device of the invention is there illustrated and generally designated by the numeral 80. This embodiment of the invention is similar in many respects to that shown in FIGS. 1 through 7 and, therefore, like numbers are used in these figures to identify like components. This apparatus is unique in that the microbore tubing used to form the body portion of the hollow cannula functions not only as a fluid delivery means, but also as a flow rate control means for controlling the rate of fluid flow from the device. Additionally, the inner body portion of the cannula is coiled in a unique manner to enhance the ability of a portion of the cannula body to move relative to the base of the device. The bore of the microbore tubing preferable is of a diameter of between about 0.005 and about 0.0002 inches.

The apparatus of this latest form of the invention includes a base 82 which cooperates with a distendable membrane 32, a barrier membrane 46, a conformable ullage 44 and a cover 84 to form a generally toroidal-shaped fluid reservoir 28, having an inlet 86 and an outlet 87 both of which communicate with a delivery cannula 88. As before, a portion of cannula 88 is receivable within a circuitous channel 90 formed in base 82. Cannula 88 has an outer segment 88o, an inner coiled portion 88i, and an enlarged diameter end portion 88a. Filter means, here provided as a porous filter 92 with fluid impermeable layer 92a (FIG. 11), is disposed between the outlet of reservoir 28 and an inlet 96 formed in enlarged diameter portion 88a of cannula 88. Also formed in the enlarged diameter portion 88a of the cannula is an outlet port 98 which communicates with inlet 86 of reservoir 28. Outlet port 98 also communicates with a fluid passageway 100 formed in enlarged diameter portion 88a, which passageway is sealed at its outboard end by a septum assembly 67 of the character previously described. Fluid introduced into the device via septum assembly 67 will flow through passageway 100 and then into reservoir 28 via inlet 86. As the fluid enters the reservoir, it will distend the distendable membrane and compresses the conformable ullage in the manner previously discussed.

Figure 10:
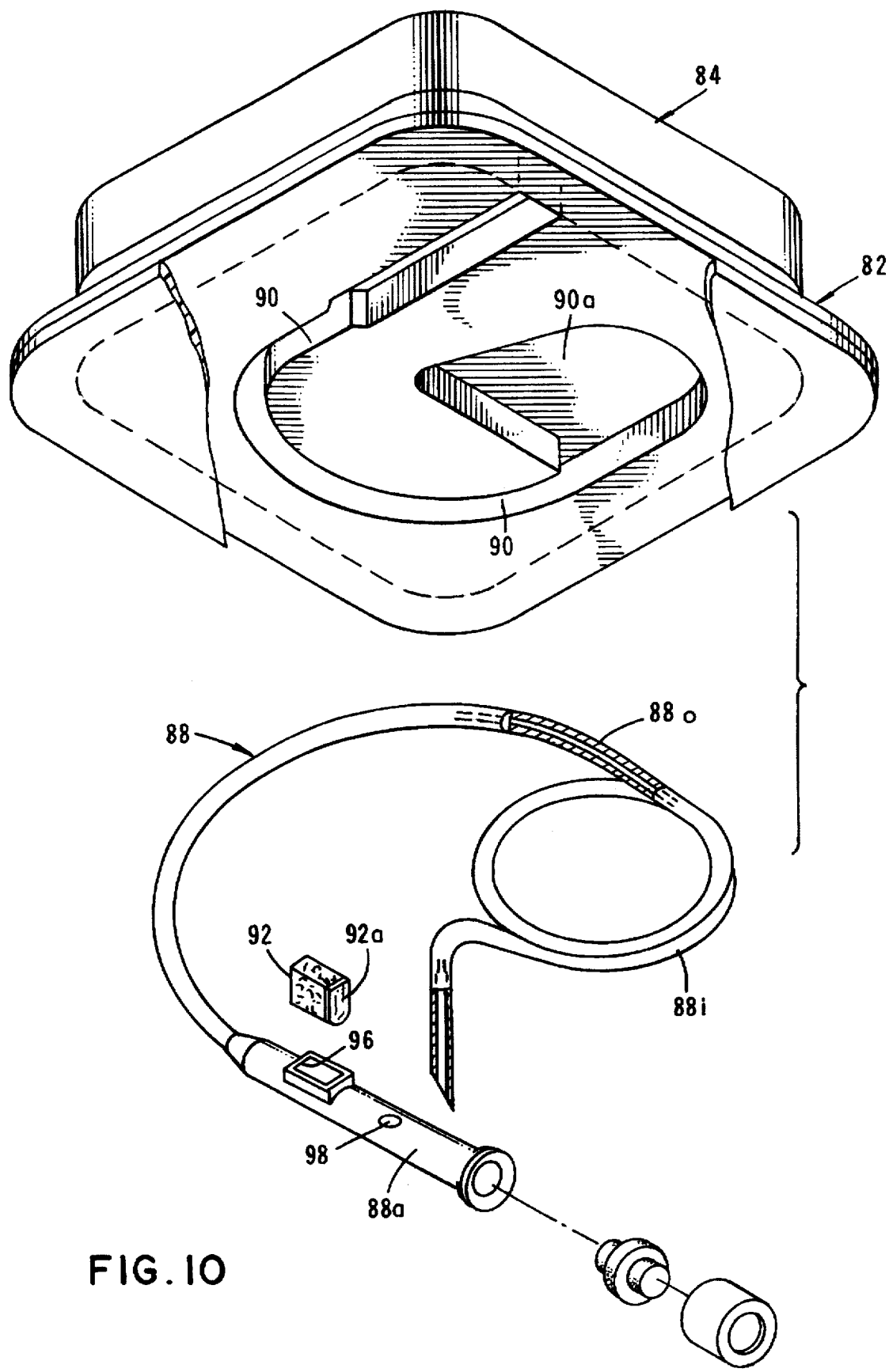
FIG. 10 is a generally perspective, exploded view of the apparatus shown in FIG. 8.

Turning particularly to FIG. 8, it is to be noted that the portion 88o of the cannula is secured in place within channel 90 by a suitable encapsulation means, such as the previously described potting compound "P". With this construction, the coiled inner portion 88i of the cannula is free to move within the portion of channel 90 designated as 90a in FIGS. 9 and 10. With this unique arrangement, normal movement by the patient will permit the cannula to move three dimensionally within channel 90a while the base remains completely stationary. Without this important feature, each movement by the patient that causes flexing of the skin, muscles and tissue and muscle could impart undesirable loosening forces to the adhesive pad which, in turn, could cause the base of the device to become separated from the patient.

Once the device has been removably interconnected with the patient, infusion of the beneficial agent contained within reservoir 28 via cannula 88 is accomplished in the manner previously described. However, in this latest embodiment of the invention, the rate of fluid flow from the device is closely controlled by controlling the size of the microbore portion 88o of the cannula which communicates with passageway 100. As before, the diameter of the bore of the microbore tubing used to construct cannula portion 88o can range from between about 0.0002 and about 0.005 inches so that the beneficial agent can be controllably diffused over relatively long periods of time up to 24 hours or longer.

Referring to FIGS. 12 through 18, yet another form of the ultra low profile device of the invention is there shown and generally designated by the numeral 110. This latest embodiment of the invention is quite similar to the embodiment shown in FIGS. 1 through 7 in that it also includes a generally toroidal-shaped, conformable ullage and reservoir (see FIG. 12). Because of the similarity of this latest form of the invention to that shown in FIGS. 1 through 7, like numerals will be used to identify like components.

Figure 12:
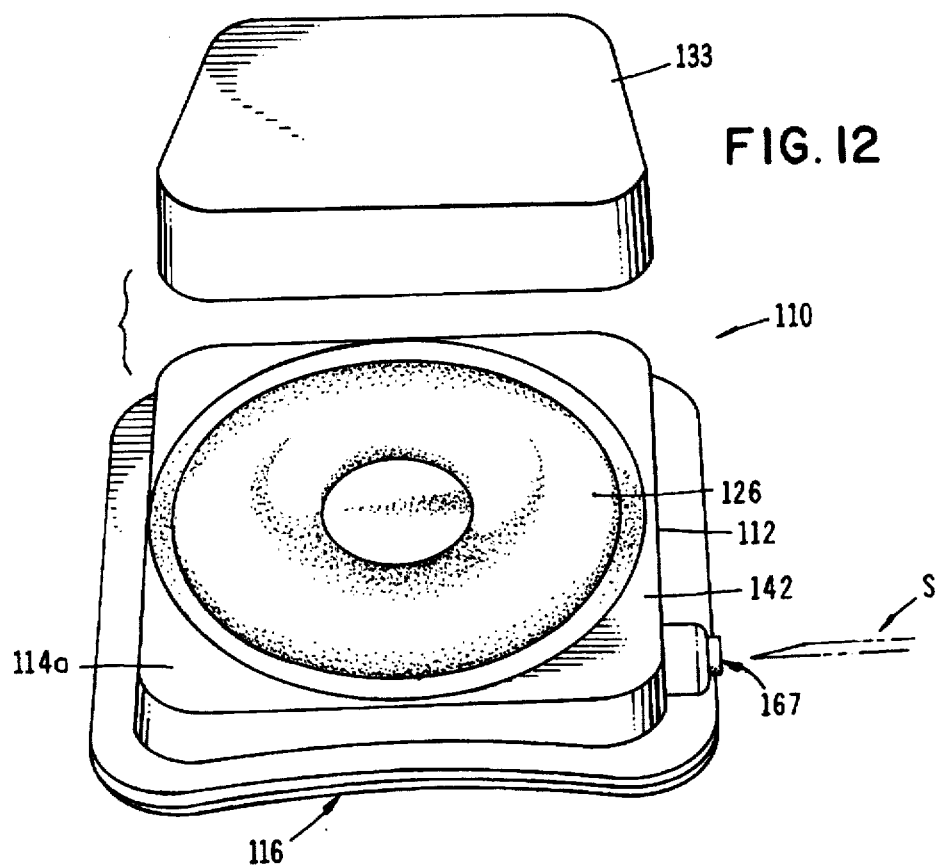
FIG. 12 is a generally perspective view of yet another form of low profile fluid delivery apparatus of the present invention.
Figure 13:
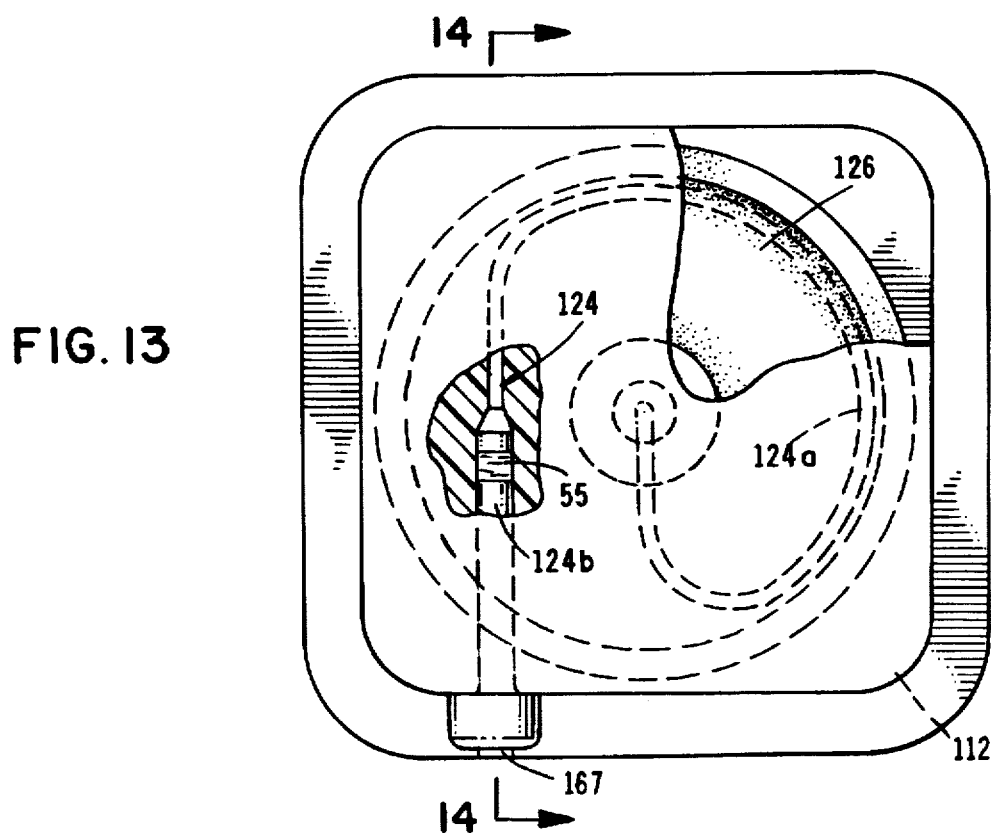
FIG. 13 is a top view of the embodiment shown in FIG. 12 partly broken away to show internal construction.
Figure 14:
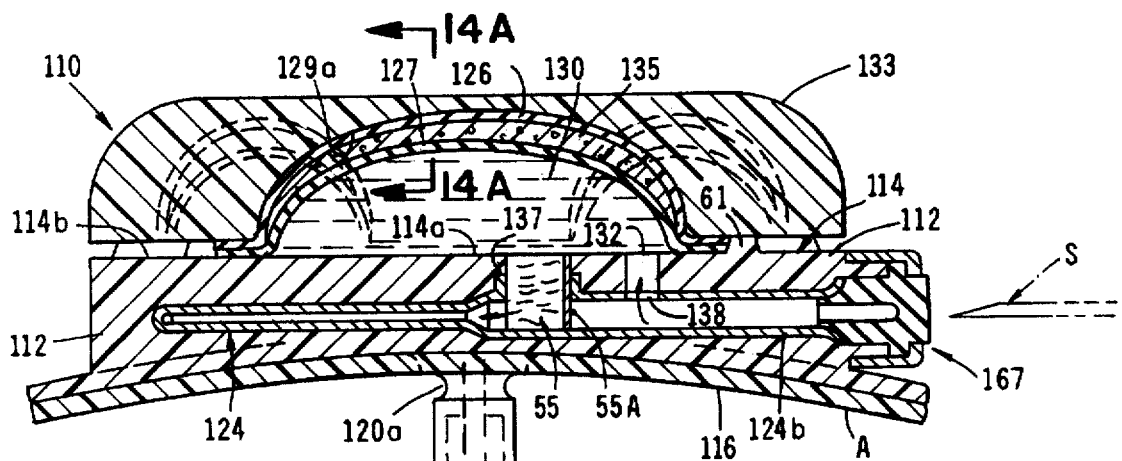
FIG. 14 is a cross-sectional view taken along lines 14—14 of FIG. 13.

As best seen in FIGS. 12, 13, and 14, the device here comprises a base 112, having an upper surface 114 including a central portion 114a and a peripheral portion 114b circumscribing central portion 114a. As before, base 112 is provided with a lower surface to which a patient interconnection means or member 116 is connected. Member 116 functions to releasably interconnect the device to the patient by means of an adhesive layer "A" provided on its lower surface. Also connected to base 112 is a protective cover means including a needle cap or sheath subassembly 119 of a construction similar to that shown in FIG. 5A. Subassembly 119 includes a protective sheath 120 within which a closure means or cap 122 is telescopically received. Cap 122 has an inner bore within which penetrable cannula portion 124c is sealably received. The upper portion of sheath 120 is provided with a serration 120a so that the sheath, along with cap 122, can be separated from the cannula at time of use.

Figure 18:
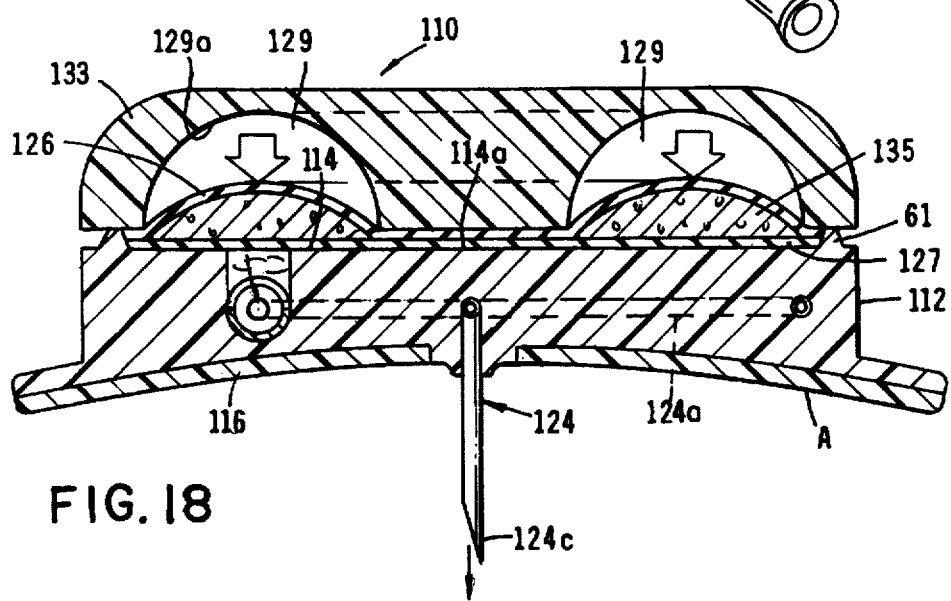
FIG. 18 is a cross-sectional view similar to FIG. 17, but showing the stored energy means having moved into a less distended configuration.

Unlike the apparatus shown in FIGS. 1 through 7, the hollow cannula or capillary 124 of this embodiment of the invention is insert molded within base 112 in the manner shown in FIG. 14. However, as in the previously described embodiments, a stored energy means or distendable membrane 126, an ullage defining means and an elastomeric barrier membrane 127 cooperate with the upper surface of base 112 to form a reservoir 130 having an inlet port 132 and an outlet port 132a (FIG. 14) which are superimposed over enlarged diameter portion 124b of cannula 124 in the manner shown in FIG. 14. The stored energy means, or distendable membrane 126 and the barrier membrane 127, both function in the same manner to accomplish the same result as previously described herein. As previously mentioned, the chamber or reservoir, which includes fluid reservoir 130, is generally toroidal in shape with the outer boundary thereof being defined by a surface 129a formed in a cover member 133 (FIG. 18).

Provided within the toroidal-shaped chamber is the previously mentioned ullage defining means for engagement with membrane 126 as the membrane moves into its distended configuration. The ullage defining means in the present embodiment, shown here as conformable mass 135, also operates in the same manner to accomplish the same result as previously described.

In this latest form of the invention, the infusion means for infusing medicinal fluids from reservoir 130 into the patient comprises the previously identified circuitously shaped hollow cannula 124. Cannula 124 includes a body portion 124a which is molded in base 112 in a manner well known by those skilled in the art. Filter means, here provided as a porous filter 55 with fluid impermeable layer 55a is disposed between the outlet of reservoir 130 and on inlet 137 formed in enlarged diameter portion 124b of cannula 124. Also formed in the enlarged diameter portion 124b of the cannula is an outlet port 138 which communicates with inlet 132 of reservoir 130. Cannula 124 also includes an outlet end, here provided in the form of the needle-like segment 124c, which extends generally perpendicularly downward from base 112 for subdermal infusion of medicinal fluids into the patient. As before, the protective sheath assembly 120 surrounds and protects segment 124c of the cannula (FIG. 14).

Figure 15:
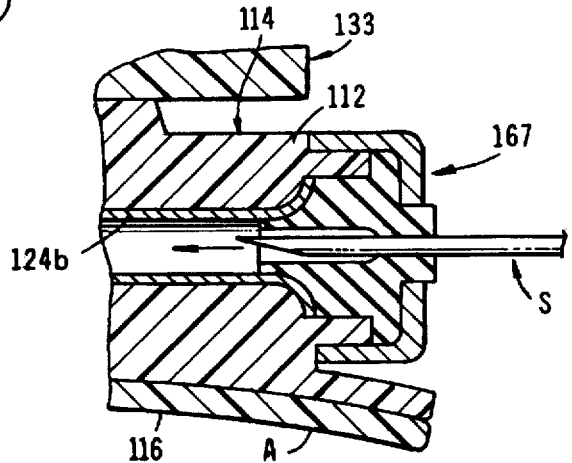
FIG. 15 is a greatly enlarged, fragmentary cross-sectional view illustrating the construction of the filling subassembly of this embodiment of the invention.
Figure 16:
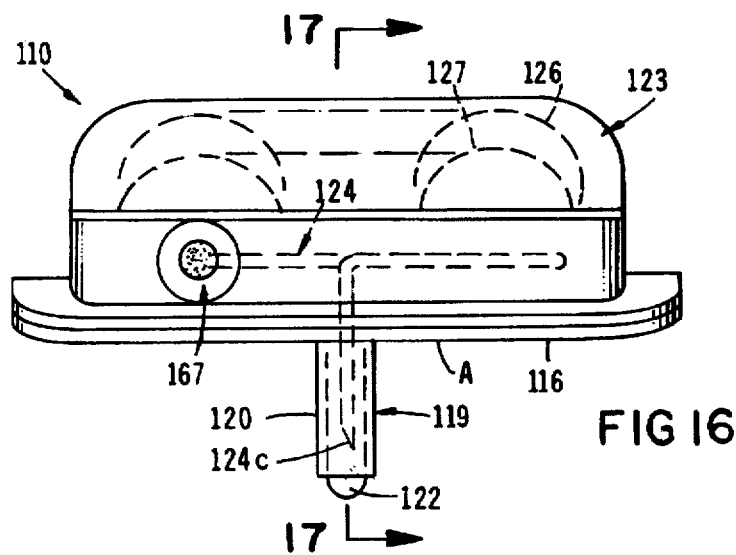
FIG. 16 is a right-side elevational view of the apparatus of FIG. 12.
Figure 17:
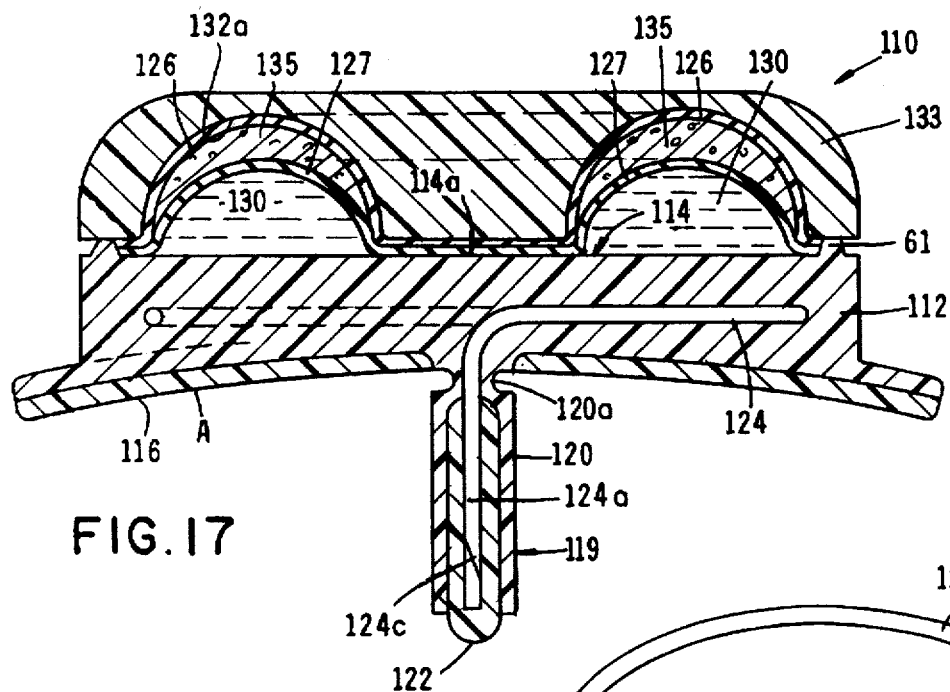
FIG. 17 is an enlarged, cross-sectional view taken along lines 17—17 of FIG. 16.
Figure 19:
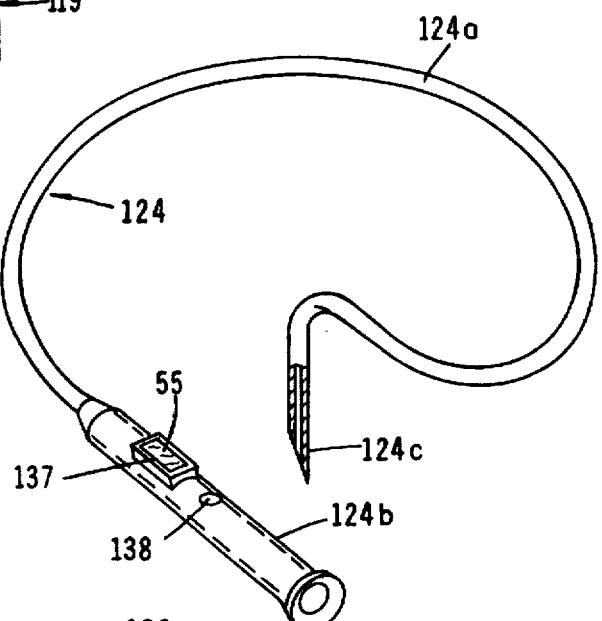
FIG. 19 is an enlarged, generally perspective view of the hollow cannula subassembly of this latest form of the invention.

Filling of reservoir 130 is accomplished in the manner previously described by introducing fluid into the reservoir under pressure via a septum assembly 167 mounted in base 112 (FIGS. 14 and 15). Using a conventional syringe assembly "S", fluid can be introduced into the enlarged diameter portion 124b of cannula 124 via the septum assembly 167. During this filling step barrier membrane 127 is distended outwardly against the conformable ullage 135 controllably moving it, along with distendable membrane 126 toward a cover 133. As the distendable membrane 126 engages the upper wall of channel 129, it will conform to the channel surface as will the upper surface of ullage 135. With this construction, when the fluid is dispensed from the device in the manner shown in FIG. 18, the conformable ullage will permit the distendable membrane to provide a constant fluid expelling pressure on the fluid contained within the reservoir throughout the fluid delivery cycle, thereby avoiding undesirable delivery rate tail off at the end of the delivery period.

As best seen in FIG. 14, during the fluid delivery step, fluid will flow from reservoir 130, through port 132a through a flow control means shown here as flow control assembly 55 then into the enlarged diameter portion 124b of cannula 124. Flow control assembly 55 is identical to that shown in FIG. 1 and functions as described herein.

Distendable member 126, along with barrier membrane 127, is secured to base 112 in the manner previously described as is cover member 133. As before, protuberance 61 also uniquely functions as a sonic energy director for the sonic weldment of base 112 and cover 133.

Figure 14A:
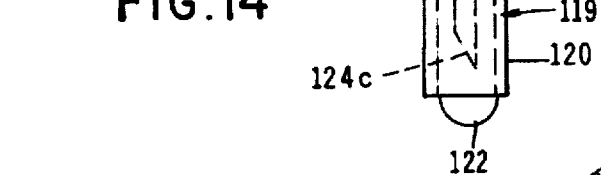
FIG. 14A is a cross-sectional view taken along lines 14A—14A of FIG. 14.

As shown in FIG. 14A, the distendable membrane 126 can comprise a laminate construction comprising first, second and third layers, or submembranes 126a, 126b, and 126c. The laminate construction provides several operational advantages as described in detail in U.S. Pat. No. 5,205,820 (see, for example, Column 17).

The device of this latest form of the invention is used in a manner similar to the apparatus shown in FIGS. 1 through 7 and, therefore, the details of operation of the device will not here be discussed.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery device for use in subdermal delivery of fluid to a patient at a controlled rate comprising:
   (a) a base having an upper surface and a lower surface engageable with the patient and a channel formed in said base intermediate said upper and lower surfaces, said channel having first and second ends;
   (b) stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration;
   (c) infusion means for infusing medicinal fluid from said fluid reservoir into the patient, said infusion means comprising a hollow cannula having:
      (i) an inlet end portion disposed proximate said first end of said channel;
      (ii) a central body portion disposed within said channel formed in said base; and
      (iii) an end portion having a first segment movably disposed within said channel and a second segment comprising a pierceable portion extending outwardly from said second end of said channel for insertion into patient; and
   (d) cannula encapsulation means for encapsulating and immovably constraining said central body portion of said hollow cannula within said channel and for dynamically supporting said end portion of said cannula.

2. A device as defined in claim 1 in which said pierceable portion of said hollow cannula extends angularly outwardly from said lower surface of said base for subdermal infusion of fluid.

3. A device as defined in claim 1 in which said channel formed in said base is generally spiral shaped.

4. A device as defined in claim 1 further including ullage defining means disposed intermediate said distendable membrane and said base for providing ullage within said reservoir, said ullage-defining means comprising a mass that is substantially conformable to the shape of said distendable membrane as said membrane tends to move toward a less distended configuration.

5. A device as defined in claim 1 further including filling means in communication with said fluid reservoir for introducing fluid into said fluid reservoir.

6. A device as defined in claim 1 further including flow control means connected to said base for controlling fluid flow toward said infusion means.

7. A device as defined in claim 6 in which said flow control means comprises a filter element for filtering the fluid flow from said reservoir.

8. A device as defined in claim 6 further including a cover sonically welded to said base.

9. A fluid delivery device for use in the subdermal infusion of medicinal liquids into a patient at a controlled rate comprising:
   (a) a base having an upper surface including a central portion and a peripheral portion circumscribing said central portion, a lower surface engageable with the patient and a generally spiral shaped channel formed in said base intermediate said upper and lower surfaces said channel having first and second ends;
   (b) stored energy means for forming in conjunction with said base, a generally toroidal-shaped reservoir having an outlet, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) ullage defining means disposed within said reservoir for engagement by said distendable membrane, said ullage defining means comprising a yieldable mass that is substantially conformable to the shape of said distendable membrane as said membrane tends to move toward a less distended configuration; and
   (d) infusion means for infusing medicinal liquids from said fluid reservoir into the patient, said infusion means having an inlet end disposed proximate said first end of said generally spiral-shaped channel and including a hollow cannula having:
      (i) a central body portion disposed within said generally spiral-shaped channel; and
      (ii) an outlet end portion, including a pierceable portion extending substantially perpendicularly outward from said lower surface of said base for insertion in to the patient.

10. A device as defined in claim 9 further including flow control means disposed between said reservoir and said inlet end of said infusion means for controlling liquid flow from said reservoir.

11. A device as defined in claim 9 further including a cover affixed to said base, said cover having a concave surface formed therein for receiving said ullage means.

12. A device as defined in claim 9 further including liquid inlet means for introducing liquid into said fluid reservoir, said liquid inlet means comprising a pierceable septum mounted in said base.

13. A device as defined in claim 12 in which said hollow cannula includes an end portion for receiving a portion of said pierceable septum.

14. A device as defined in claim 12 further including a protective sheath removably connected to said base for surrounding and protecting said pierceable portion of said hollow cannula.

15. A device as defined in claim 14 further including a cannula closure telescopically receivable within said protective sheath, said cannula closure having a central bore for receiving said pierceable portion of said hollow cannula.

16. A low profile device for use in infusing medicinal fluid into a patient at a controlled rate comprising:
   (a) a thin base having an upper surface including a central portion and a peripheral portion circumscribing said central portion, a lower surface engageable with the patient and a circuitous channel formed in said base intermediate said upper and lower surface, portions of said channel being disposed proximate said central portion and said peripheral portion, said channel having first and second ends;
   (b) stored energy means for forming in conjunction with said base a reservoir, said reservoir having a fluid inlet and a fluid outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration;

(c) ullage defining means disposed within said reservoir for engagement by said distendable membrane, said ullage defining means comprising a flowable mass;

(d) fill means in communication with said reservoir of said device for filling said reservoir; and (e) infusion means for infusing medicinal fluid from said reservoir into the patient, said infusion means comprising a hollow cannula having:
  (i) a body portion disposed within said circuitous channel formed in said base; and
  (ii) an outlet end provided in the form of a pierceable portion extending outwardly from said second end of said channel for insertion into the patient.

17. A device as defined in claim 16 in which said pierceable portion of said infusion means extends outwardly in a direction substantially perpendicular to said lower surface of said base for insertion into a patient for subdermal infusion of fluid into the patient.

18. A device as defined in claim 16 in which said hollow cannula includes a microbore fluid flow portion.

19. A device as defined in claim 16 in which said ullage defining means comprises a gel disposed in said reservoir that is substantially conformable to the shape of said distendable membrane as said membrane tends to move toward a less distended configuration.

20. A device as defined in claim 16 in which said fill means comprises a pierceable septum mounted within said base.

21. A device as defined in claim 16 further including filter means connected to said base for filtering fluid flowing from said fluid reservoir toward said outlet end of said hollow cannula.

22. A device as defined in claim 21 in which said hollow cannula includes an enlarged diameter portion having an opening and in which said filter means comprises a filter partially received within said opening provided in said enlarged diameter portion of said cannula for filtering fluid flowing toward said pierceable portion of said cannula.

23. A device as defined in claim 21 in which said hollow cannula is generally serpentine in shape and is at least partially received within said circuitous channel formed in said base.

* * * * *